United States Patent [19]
Glazer et al.

[11] Patent Number: 5,473,537
[45] Date of Patent: Dec. 5, 1995

[54] METHOD FOR EVALUATING AND REVIEWING A PATIENT'S CONDITION

[75] Inventors: William M. Glazer, Menemsha, Mass.; Geoffrey V. Gray, Fairfield, Conn.

[73] Assignee: Psychresources Development Company, North Haven, Conn.

[21] Appl. No.: 420,854

[22] Filed: Apr. 12, 1995

Related U.S. Application Data

[63] Continuation of Ser. No. 100,566, Jul. 30, 1993, abandoned.
[51] Int. Cl.⁶ .................................................. G06F 159/00
[52] U.S. Cl. ......................... 364/419.2; 128/630; 128/732
[58] Field of Search ..................................... 128/732, 630; 364/419.2; 600/26, 27

[56] References Cited

U.S. PATENT DOCUMENTS 4,489,387  12/1984  Lamb et al. ............................ 364/514

OTHER PUBLICATIONS

Arbor, "Methodological Aspects of Onset Assessment in Schizophrenia", Univ. Microfilms, Ann Arbor, Mich. 1978 (125p.); Dialog File 73 Acc. #9567492.

*Primary Examiner*—Gail O. Hayes
*Assistant Examiner*—Frantzy Poinvil
*Attorney, Agent, or Firm*—Bachman & Lapointe

[57] ABSTRACT

A method for evaluating and/or reviewing a patient's condition comprises the steps of: collecting clinical data relevant to a determination about the propriety of a particular level of care for a patient; generating a behavioral severity series for the patient; and deriving a recommended treatment intensity from the behavioral severity series. The method is preferably performed using a computer to collect the clinical data. The computer can be programmed to automatically generate the behavioral severity series and derive the recommended treatment intensity for the patient.

16 Claims, 4 Drawing Sheets

METHOD FOR EVALUATING AND REVIEWING A PATIENT'S CONDITION

This is a Continuation, of application Ser. No. 08/100,566, filed Jul. 30, 1993, now abandoned.

BACKGROUND OF THE INVENTION

The present invention relates to a method for enabling medical care providers, particularly, mental health practitioners and providers, to evaluate and review the condition of a patient and a proposed course of treatment for that patient.

The quality of medical care is determined in large part by the quality of the decisions that determine what actions are taken. Psychiatry, like medicine in general, has done little to reduce the variance in clinical decision making. Consider the admission data for psychiatric illness as displayed in FIG. 1. As shown therein, admission rates for psychiatric care may vary on the order of 16 to 1. Even between Health Maintenance Organizations (HMO's), the variation rate may exceed 8 to 1. Inasmuch as variances in admission rates reflect normative judgements concerning medical necessity, it can be seen that there is considerable variability in actual clinical practice. The fact is that psychiatrists like other physicians frequently make decisions based upon extra-clinical considerations. These include financial incentives, pressure from the patient or his/her family, specialist enthusiasm, the convenience of the doctor and/or the patient, the failure of non-medical providers to appropriately interface with psychiatrists or vice-versa, cultural imperatives to "do something", and malpractice concerns among others. In sum, one can say that hospital-based utilization is, to a significant extent, due to the practice patterns of local psychiatrists as well as the range and availability of the treatment resources in a community's system of care and not to the epidemiological incidence of psychiatric disease.

These findings raise concerns about the high incidence of false positives, that is, overtreatment in the form of over-utilization of hospital based treatment. Also, of concern, is the recent tendency to withhold hospitalization treatment as a result of a system which frequently rewards providers for withholding care or for providing less intensive and costly care than is necessary.

There clearly is a need for a product to assist mental health professionals in precertification decisions.

SUMMARY OF THE INVENTION

Accordingly, it is an object of the present invention to provide a method for precertifying routine and acute patients in private and public managed care settings by prospectively assessing the appropriateness of the recommended psychiatric treatment.

It is a further object of the present invention to provide a method as above which compares a patient's clinical profile with consensus standards of care.

It is yet a further object of the present invention to provide a method as above which provides physicians with an objective tool to analyze clinical data and a normative database against which to evaluate treatment options to allow allocation of care.

These and further objects and advantages to the method of the present invention will become more clear from the following description and drawings wherein like reference numerals depict like elements.

The method of the present invention as described herein readily attains the foregoing objects and advantages. The method of the present invention broadly comprises the steps of: collecting clinical data relevant to a determination about the propriety or necessity of a particular level of care for an individual; generating a behavioral severity series for that individual using the collected data; and deriving a treatment intensity based upon the behavioral severity series. The clinical data which is collected preferably includes information about the individual's tendency towards dangerous behavior, the individual's social performance, the individual's substance abuse risk, the provider's opinion as to imminent danger, and the social resources available to the individual. After the foregoing information is collected, it is rated in accordance with a predetermined rating system. The behavioral severity series generated from the rated information forms a profile of the individual undergoing evaluation. After the profile has been generated, it is correlated with different levels of potential care to determine the appropriateness of a particular course of treatment.

The method of the present invention is preferably performed with the aid of a computer.

The method of the present invention readily lends itself to several applications. For example, it may be used as part of a precertification assessment for a patient. Alternatively, it may be used as part of a treatment assessment after a patient has been admitted to a hospital or other health care facility. Still further, it may be used as part of a review program for a health maintenance organization to assess the appropriateness of treatments being recommended by doctors participating in the health maintenance organization network.

Other details and applications of the method of the present invention are set forth in the following description.

DETAILED DESCRIPTION

As previously discussed, the present invention is directed to a method for evaluating and reviewing the condition of an individual or patient and a particular level of care or treatment for that individual. The care or treatment may have taken place and the user of the method may be evaluating the reasonableness or propriety of the care or treatment or the care or treatment may be a future event which is being precertified.

As previously mentioned, the method of the present invention is preferably performed with the aid of a computer. When a computer is used, the method of the present invention may be embodied in the form of a computer program. The program may be in any desired language and may be implemented on any desired computer including personal computers, laptop computers, or mainframe computer systems.

The method of the present invention comprises the steps of collecting clinical data about an individual which is relevant to a determination of the propriety or necessity of a particular level of care, generating a behavioral severity series for the individual whose case is being assessed, and deriving a treatment intensity based upon the behavioral severity series for that individual.

Figure 2:
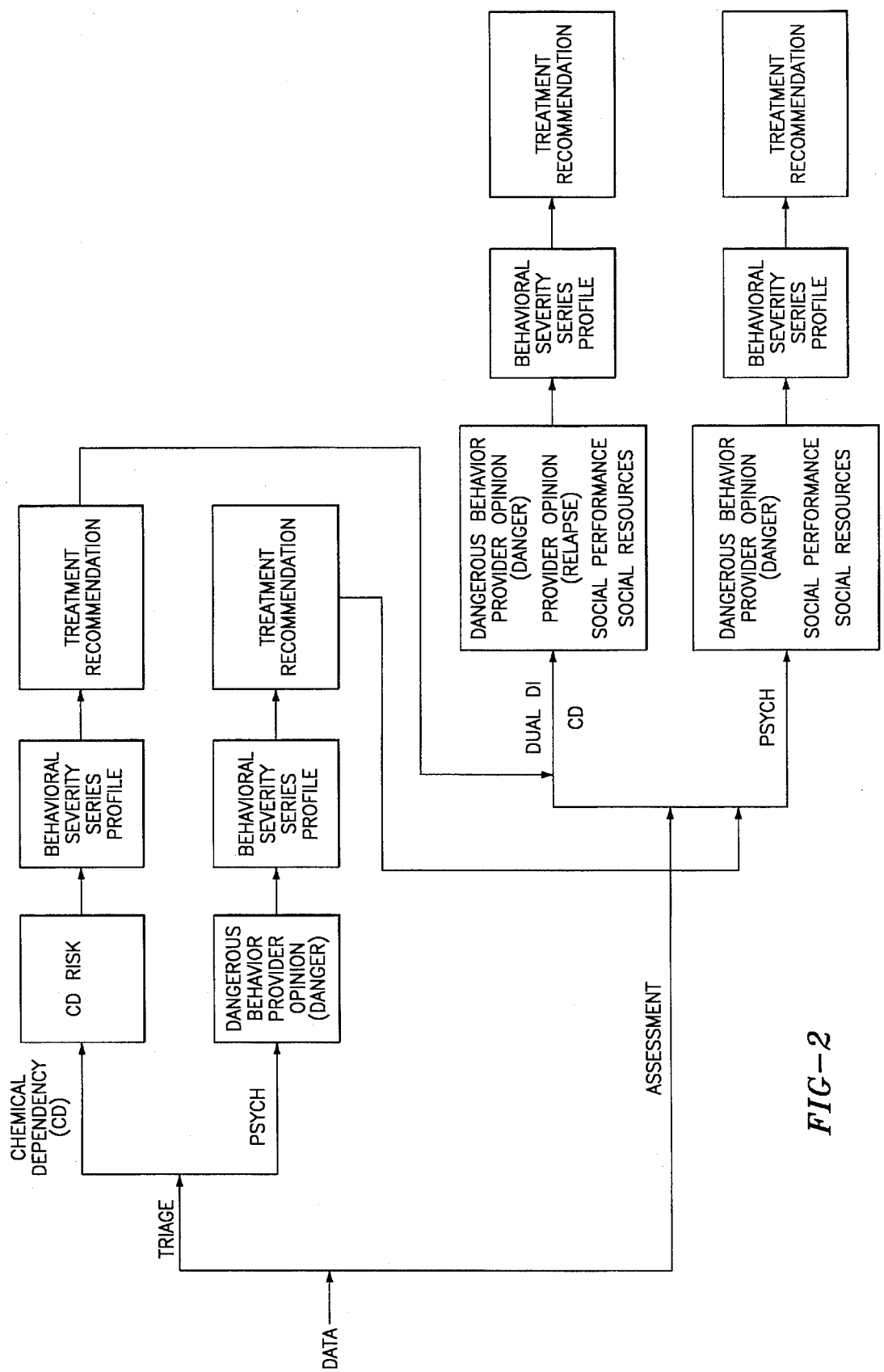
FIG. 2 is a flow chart showing the steps of the method of the present invention.

FIG. 2 illustrates a flow chart showing the method of the present invention. As shown therein, clinical data or information can be gathered about the individual from treating clinicians including psychiatrists. This initial information may be characterized as either a triage evaluation or an assessment evaluation. Triage evaluations are made when information is deficient and/or the presenting clinical problem is emergent in nature. Assessment evaluations are made when pertinent clinical information is complete. If the triage or assessment relates to a chemical dependency (CD) problem, then a CD risk scale is preferably applied to generate the behavioral severity series for the individual. If the triage or assessment relates to another type of psychiatric problem, then a dangerous behavior risk scale is applied to generate the behavioral severity series for the individual. After the behavioral severity series is generated, a profile of the individual is generated. From this profile, a treatment or level of care recommendation is formed.

If desired, an assessment of the level of care for the individual under treatment can be conducted after a triage evaluation has taken place. This typically would occur when all the information needed to make a full assessment is obtained. As can be seen from FIG. 2, the treatment recommendation from the triage evaluation can form part of the input into assessment analysis.

The clinical data about the individual which is collected as an initial step comprises five clinical elements which underlie psychiatric decision making. These five elements provide the dimensions through which behavioral data is gathered in a standardized way. The elements are: (a) dangerous behavior; (b) provider opinion about imminent danger; (c) social performance; (d) social resources; and (e) substance abuse risk.

The clinical data which is gathered about the dangerous behavior dimension preferably applies to behavior during a period of time, i.e. seven days, immediately preceding the time of assessment. Past history of dangerous behavior can be recorded and considered but typically is not part of the dangerous behavior information used to form the behavior severity series. Dangerous behavior of particular interest includes intentional behaviors, i.e. behavior which exhibits an idea, plan or activity related to suicide or verbal or physical aggression towards other people or objects, and reckless endangerment behavior. The abrupt onset of psychoticism is also considered as dangerous behavior. Examples of reckless endangerment behavior include: (a) driving under the influence of substances; (b) carrying a loaded weapon out of peer pressure or to make an impact; and (c) placing oneself in dangerous areas where there is a risk of assault or battery. Willful or criminal behavior unrelated to a psychiatric condition is not considered dangerous behavior.

Questions which may be asked to gather clinical data about dangerous behavior include the following:

(a) what has (s)he done in the last 7 days that might be considered dangerous;

(b) was this intentional;

(c) does the patient have ideas about committing a dangerous act;

(d) does the patient have a plan to commit a dangerous act;

(e) describe why it is felt that the patient is imminently dangerous;

(f) what treatment result (to self or others) from the behavior;

(g) what harm resulted (to self or others) from the behavior;

(h) if behavior is considered reckless endangerment, what has caused the person to behave recklessly;

(i) does the person have access to lethal weapons;

(j) what is the worst behavior that this patient has exhibited in his or her life; and (k) when did such behavior take place?

In accordance with the present invention, a three point rating system can be employed to evaluate the risk of dangerous behavior. In such a system, a numerical value of 1 can be assigned to low-risk situations, a numerical value of 2 can be assigned to moderate-risk situations, and a numerical value of 3 can be assigned to high-risk situations. Anchor points made up of specific behavioral descriptions are associated with each numerical value. It should be recognized of course that other rating systems may be use if desired.

A low-risk situation is usually associated with the person who has ideation about a dangerous activity but has no plan and has exhibited no action related to that ideation.

A moderate-risk situation is the person with both ideation and a plan but who has exhibited no dangerous action. Such persons may or may not have exhibited preparatory action such as writing a note, purchasing a gun, etc. Preparatory action is a measure of the patient's intention, but it does not in and of itself constitute "dangerous behavior". A reckless endangerment person who is chronically demented and might or will get into an accident without supervision can be rated here.

A high-risk situation is seen in any recent physical activity (intentional or reckless endangerment) involving direct (actual) harm to self, others or property. An individual who has recently exhibited dangerous behavior and currently exhibits ideation is generally rated in this category. The abrupt onset of psychosis is also rated here.

Along with clinical data about dangerous behavior, information which constitutes a provider's opinion about the dangerous behavior is gathered. As used herein, the term "provider" means a therapist, a doctor, a nurse, etc. This information is deemed to be significant because it has been found to be a key dimension in the determination of the level of dangerousness. In this evaluation, the provider assesses the alliance with the individual in terms of his/her ability to contract for safety. The patient is deemed to "contract for safety" when he or she agrees not to behave in a manner that is harmful to self, others or property until the next time (s)he is evaluated by the provider.

Probative questions used to gather the necessary information may include:

(a) is the patient able to contract for safety;

(b) tell me what the patient says when you ask him/her to agree not to do anything at this time;

(c) has the patient ever broken a contract for safety in the past;

(d) what are your feelings about this patient contracting for safety; and (e) what are the patient's relatives saying about him/her contracting for safety?

Here again, a rating system is employed to evaluate the answers to these questions. The rating system may consist of the following:

3—a poor alliance seen when the evaluator concludes, after examining the patient, that he or she is unable to contract for safety;

2—a questionable alliance seen when the patient who expresses ambivalence about their ability to contract for safety or when the evaluator is not able to contract; and 1—a good alliance seen when the evaluating mental health professional determines that the patient is able to contract for safety and believes that the patient is reliable in their willingness.

Figure 1:
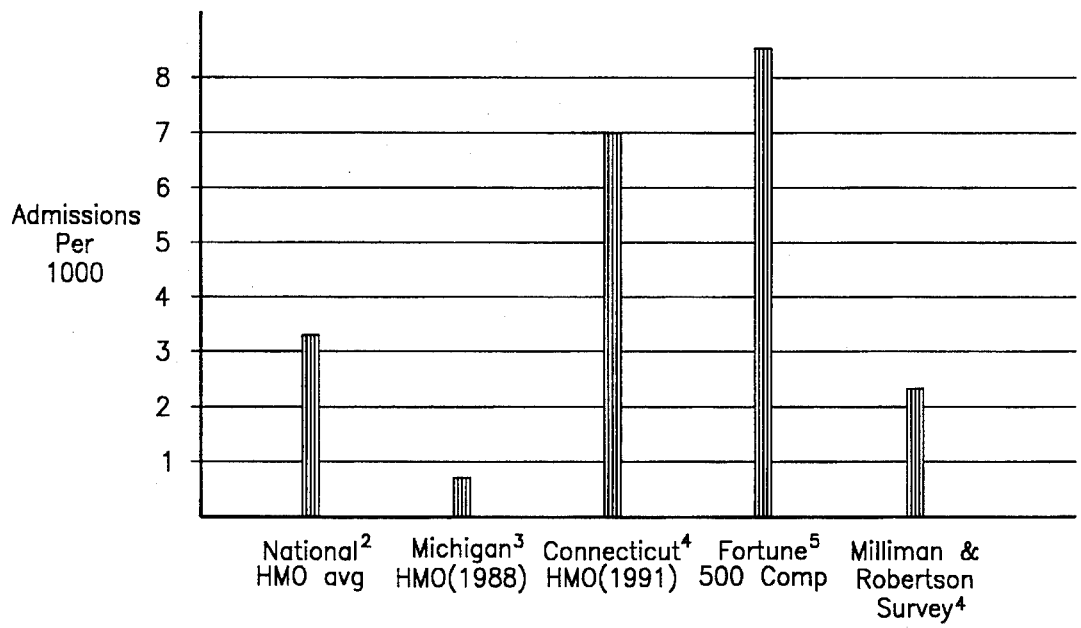
FIG. 1 is a graph showing comparisons of psychiatric inpatient utilization rates.
Figure 3:
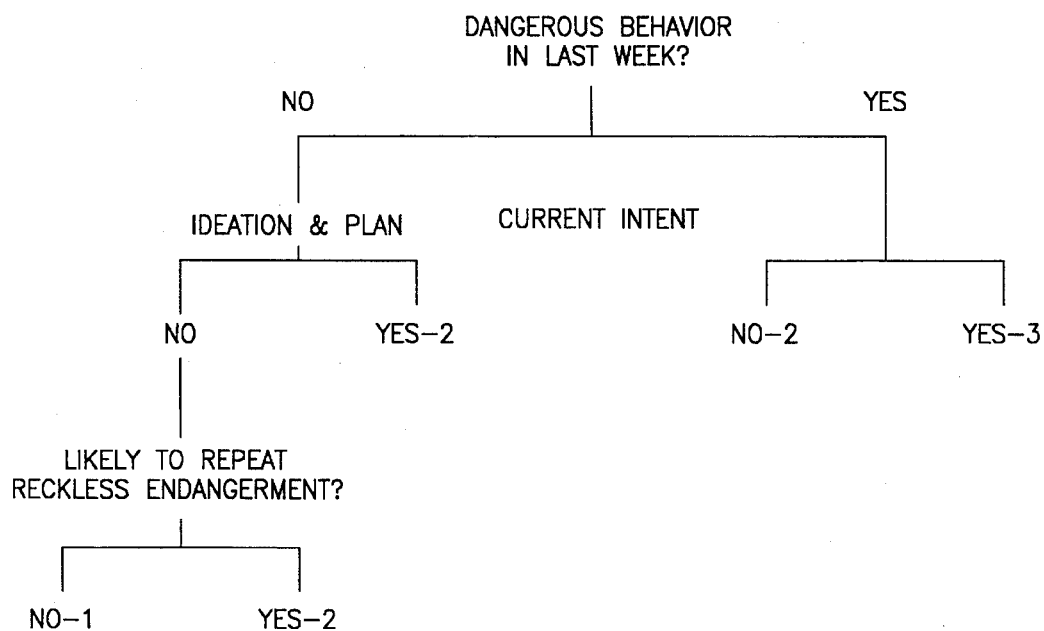
FIG. 3 is a flow chart illustrating how dangerous behavior can be rated.

FIG. 3 illustrates a flow chart showing how dangerous behavior can be rated. Table I illustrates how the aforementioned behavior and provider opinion ratings allow an overall assessment of the level of dangerous behavior for the patient.

TABLE I

| | BEHAVIOR | | |
|---|---|---|---|
| | Low-Risk 1 | Moderate-Risk 2 | High-Risk 3 |
| PROVIDER OPINION | | | |
| Good 1 | 1 | 2 | 2+ |
| Questionable 2 | 1 | 2+ | 3− |
| Poor 3 | 2 | 3− | 3 |

After dangerous behavior has been assessed, clinical data about social performance, i.e. the work role of the individual, preferably within the last month, is gathered. Typically, there are four types of work roles. They are: (1) worker; (2) student; (3) homemaker; or (4) no role.

Information which is gathered about this factor includes information about the work role of the individual: (a) do you work at a paid job; (b) are you primarily responsible for homemaking tasks; and (c) are you a matriculating student. With respect to each job, information is also gathered about the time lost, sources of friction, and adequacy of performance. For example, if the individual indicates that he/she is a worker, then information is ascertained about such matters as: missed time at work; the reasons for the missed time; how many days of missed time; friction with supervisor, co-worker or customers; do you get angry at work; do you argue much at work; have there been any open disagreements; have you been doing your job well; and have you had trouble keeping up with your work. Questions of a similar nature are asked of individuals who indicate that they are a student or a homemaker.

If the individual indicates that he/she has no role, then information may be ascertained about disability status and/or unemployment status of the individual.

Once again, a rating scale is used to rate the social performance of the patient. In a preferred embodiment, the scale for this factor is as follows:

3—Extreme
  (a) Worker has been asked to stop or has ceased working because of poor performance related to psychiatric/CD condition; and/or experiences extreme friction with other people at work.
  (b) Student has been expelled or placed on academic probation because of poor academic performance or extreme friction with other people.
  (c) Homemaker unable to perform usual household tasks because of psychiatric/CD condition.
  (d) No role—the person is the breadwinner but his/her psychiatric illness prohibits job seeking behavior.

2—Moderate to marked impairment
  (a) Worker: at least one instance in which patient was told (s)he was not performing well or patient has been warned that job is in jeopardy or that a formal job action may be initiated; some time lost (>10%) in the last month due to psychiatric or CD disorder; no time lost but there is moderate friction; and/or failed drug screen test.
  (b) Student: at least one instance in which patient was told by a teacher that (s)he was not performing well or was a source of friction; has been warned that standing in school is in jeopardy; and/or some time lost in the last month due to psychiatric or CD disorder.
  (c) Homemaker: at least one instance in which patient was told by someone in the home that (s)he was not performing well or patient requires help in completing usual tasks.
  (d) No role: the person is not the breadwinner but his/her psychiatric illness prohibits job seeking behavior; or, the person is disabled and unable to meet job requirements.

1—Some impairment (but no lost time) because of psychiatric/CD problems but no feedback from others.

Another measure of social performance which has been found to be significant is the quality of the relationship that the patient has had within a certain time period, e.g. the last month with a key person and/or others. This is known as the interpersonal role dimension. The key persons of interest can include a spouse or conjugal partner, a parent, a sibling, an adult child, and/or significant others i.e., non-relatives, therapists.

The key areas of interest in this dimension for which clinical data is collected are communication and friction. Typical probes for communication are: during the last month have you been able to talk easily with the key person; when was the last time you talked about your feelings and problems; and/or are there things that you feel you should talk about but don't. Typical probes for friction are: how have you and the key person been getting along; are there things that the key person does that makes you angry; do you argue much; have there been open disagreements; and/or is there anyone you avoid because you know that you'll get into an argument.

Once again, a rating scale is employed to quantify this factor. A typical scale may look like the following:

3—patient or individual can never talk about feelings and problems when appropriate; and/or extreme friction in interpersonal role or avoids/avoided by others because of psychiatric/cd behaviors. Severe dysfunctional relationship is evident;

2—patient or individual usually cannot talk about feelings and problems when appropriate; and/or moderate friction and/or minimizes many contacts as a consequence of psychiatric/CD behavior; and 1—patient sometimes can and sometimes cannot communicate feelings and problems; and/or mild friction related to substance abuse.

A third social performance measure involves changes in functioning for the patient for a designated time period.

Functioning is the reviewer's or provider's overall judgement of the patient's psychological, social and occupational status during the designated time period. This assessment is typically the judgement of a reviewing clinician. However, it can be rated like the other factors. A typical scale may be:

3—severe deterioration from usual functioning;
2—moderate deterioration from usual functioning;
1—mild or no change.

To evaluate the overall social performance factor, one may use a multi-dimensional matrix which takes into account work role performance, interpersonal role performance and degree of deterioration ratings. Such a matrix may look like the following:

TABLE II

|  | Degree of deterioration | | |
| --- | --- | --- | --- |
|  | Mild | Moderate | Severe |
| Severity | | | |
| 3,3[1] | II | III | III |
| 3,2 | II | III | III |
| 3,1 | II | III | III |
| 2,3 | II | III | III |
| 2,2 | I | II | II |
| 2,1 | I | I | I |
| 1,3 | II | II | II |
| 1,2 | I | I | I |
| 1,1 | I | I | I |

[1]First number = Work Role Performance Score; Second Number = Interpersonal Role Performance.

The fourth element to be evaluated in the method of the present invention is social resources available to the individual. The focus of this assessment is the patient's recovery environment which includes (1) key persons and other social and interpersonal aspects of the recovery environment and (2) the available program(s) in the patient's community. With respect to key person(s), emphasis is placed on two aspects of that person in the patient's life at the time of the crisis: (a) the availability of such a person; and (b) the degree to which they are competent to support the patient at this time of behavioral crisis. Competency of the key person refers to their ability to read cues related to the patient's mental status and to provide the patient with support, structure and guidance and feedback that will, in conjunction with the assigned treatment, allow him/her to improve.

Typical areas to be probed in gathering the information for this factor are (1) involvement of the key person, i.e. who is the most important person in your life now; does that person live with you; how much time does that person spend with you; is that person willing to watch you and supervise any medication, etc; (2) recovery environment, i.e. where does the patient live; is the mortgage/rent paid; would loss of income mean loss of living arrangement, what are the stressors in the living environment; and (3) available programs.

Again, a rating system can be applied to describe this factor. The rating system may be:

3—key person(s) not available, and/or key person not competent to support patient, and/or patient has lost his/her living arrangement and faces homelessness unless alternate arrangement can be provided;
2—key person(s) available part time to support, and/or key person not entirely competent to support the patient; and/or patient's living arrangement is stable but their are "noxious stimuli" in the environment that threaten his/her immediate recovery from this acute condition; and
1—key person(s) available full time and competent to support; and/or living arrangement is good enough to support the patient's recovery from this acute episode.

Figure 4:
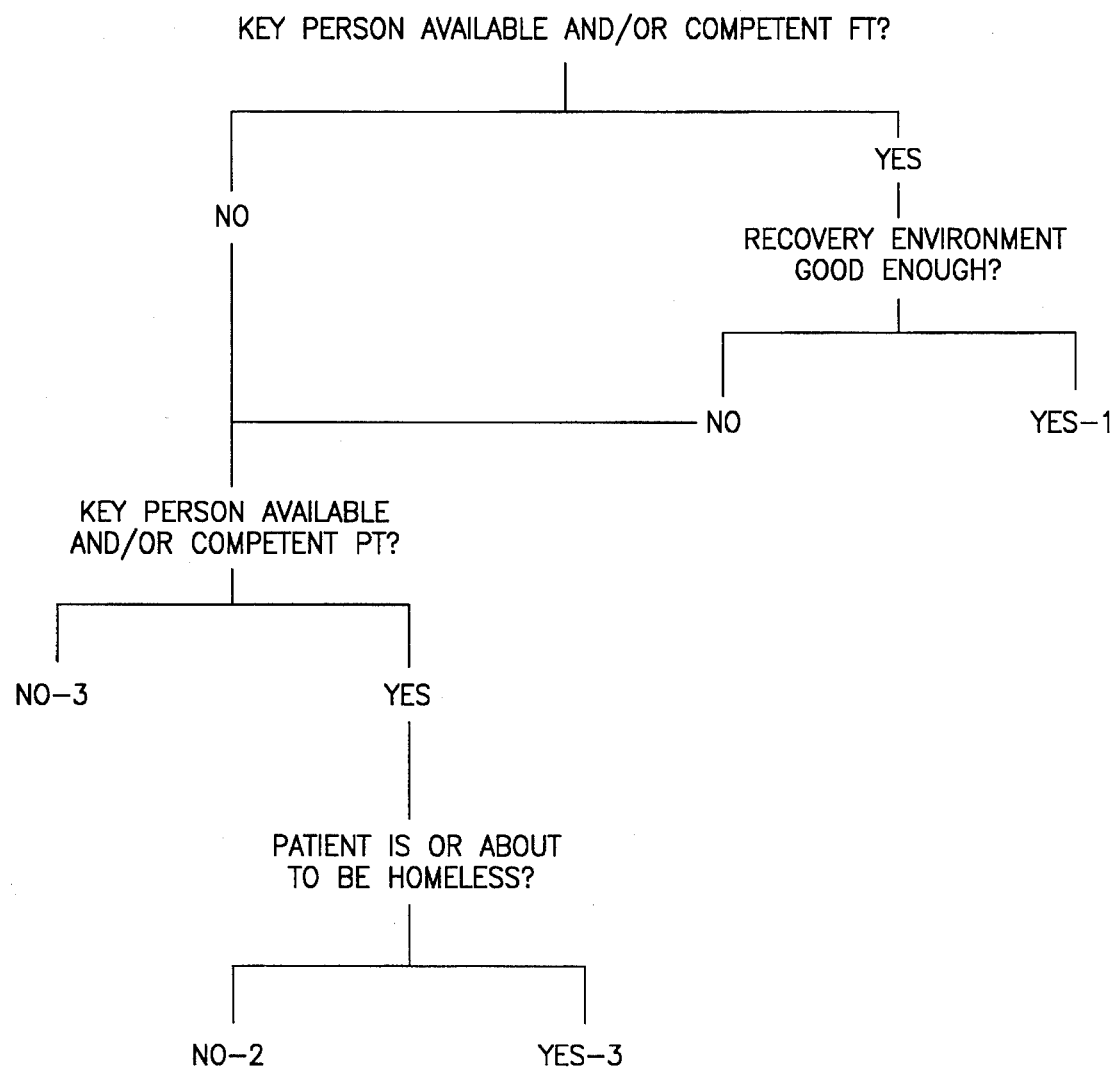
FIG. 4 is a flow chart illustrating how social resources can be rated.

FIG. 4 illustrates a flow chart showing how the rating system for the social resources factor can be applied.

The final factor to be evaluated is substance abuse risk. For this factor, information is gathered about such things as chemical dependency, i.e. has the patient used a drug or other controlled substance within a specified time period; has the patient been diagnosed as chemical dependent; are there signs of severe withdrawal; is there a history of severe withdrawal.

Again a rating system can be used to assess this factor. The rating system may be:

3—High Withdrawal Risk
  (a) signs of "severe" withdrawal are present;
  (b) presence of "common" signs of withdrawal and resting pulse >110 per minute or resting blood pressure >160/110;
  (c) some common signs currently and a history of "severe" signs and symptoms with withdrawal.
2—Moderate Withdrawal Risk
  (a) substance present in blood and/or signs of "common" withdrawal are present.
1—Low Withdrawal Risk
  (a) substance use has ceased a specified time period before assessment; and
  (b) absence of "common" signs or symptoms; and/or
  (c) no history of "common" signs and symptoms with withdrawal.

Figure 5:
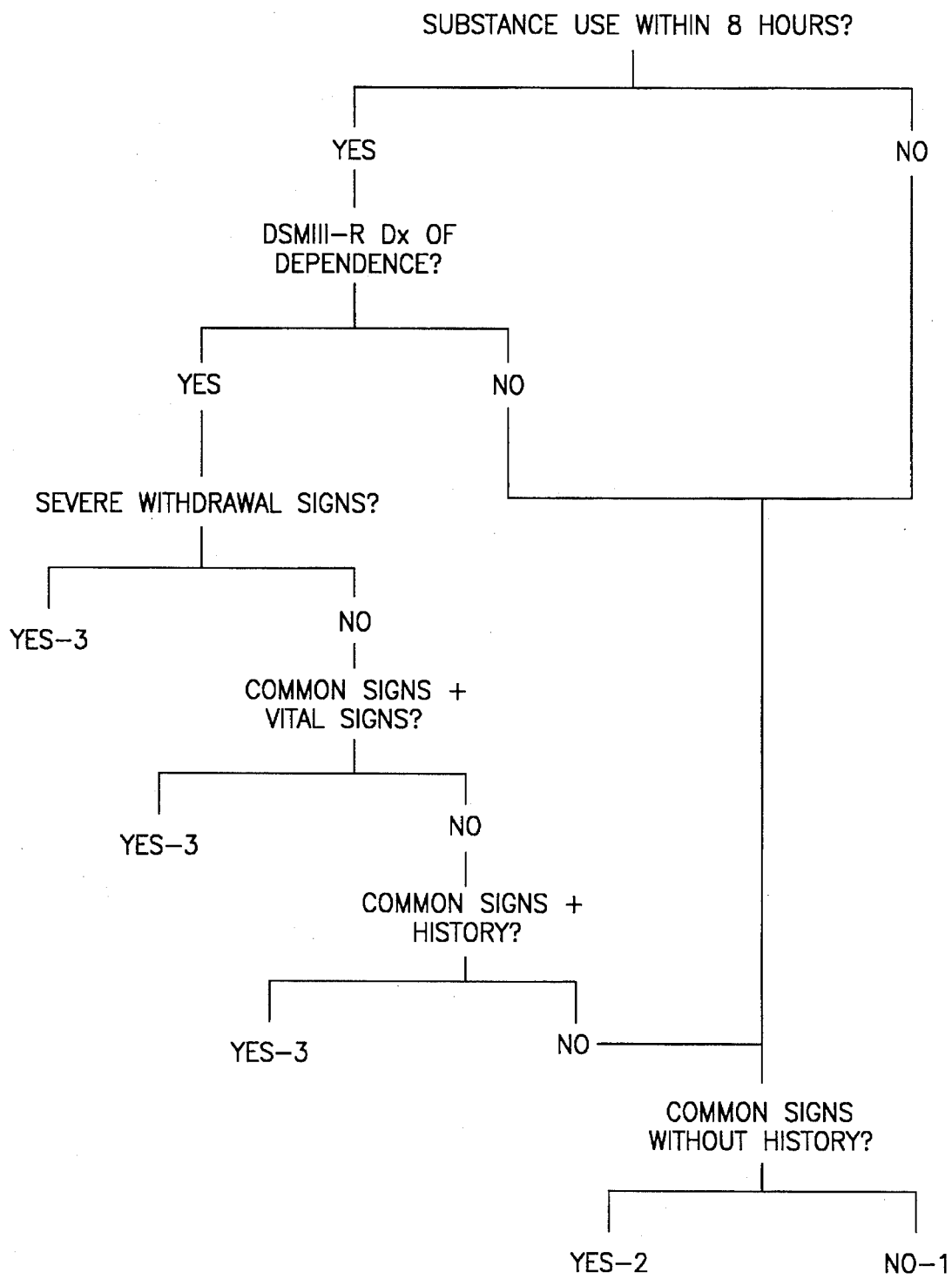
FIG. 5 is a flow chart illustrating how substance abuse risk can be rated.

FIG. 5 illustrates a flow chart of how the rating system is used in connection with this factor.

After these five factors have been assessed and the ratings completed, the method user has before him or herself a behavioral severity series for the individual or patient being assessed. The level of treatment for that particular individual or patient is determined by this behavioral severity series.

The levels of treatment which are available may also be designated from 1 to 3 with (a) 3 being acute inpatient care, (b) 3− holding bed, (c) 2++ residential non-hospital, (d) 2+ partial hospital, (e) 2 being diversion care, (f) 1+ being high intensity outpatient care; and (g) 1 being standard outpatient treatment. For substance abuse illnesses, the treatment scale may be: (a) 3− inpatient detoxification care; (b) 3− non-hospital acute detox; (c) 2++− residential therapeutic community care; (d) 2+ partial hospital; (e) 2 diversion care including medically managed outpatient care; (f) 1+ intensive outpatient; and (g) 1− standard outpatient care.

To determine or derive a recommended level of treatment, a matrix is developed which takes into account all of the ratings of the five factors and a weighing of those factors. In formulating a particular matrix to be used, particular factors may be given a weight greater than other factors. No one dimension by itself determines treatment assignment; rather it is their merged overall severity that determines treatment assignment.

A matrix scheme which can be employed with the method of the present invention is as follows:

| Risk Behav | Alliance | Soc Perf | Resource | Withdrawal Potential | TREATMENT INTENSITY |
| --- | --- | --- | --- | --- | --- |
| 1 | 1 | 1 | 1 | 1 | 1 |
| 1 | 1 | 1 | 1 | 2 | 2 |
| 1 | 1 | 1 | 1 | 3 | 3 |

| Risk Behav | Alliance | Soc Perf | Resource | Withdrawal Potential | TREATMENT INTENSITY |
|---|---|---|---|---|---|
| 1 | 1 | 1 | 2 | 1 | 1 |
| 1 | 1 | 1 | 2 | 2 | 2 |
| 1 | 1 | 1 | 2 | 3 | 3 |
| 1 | 1 | 1 | 3 | 1 | 1 |
| 1 | 1 | 1 | 3 | 2 | 2 |
| 1 | 1 | 1 | 3 | 3 | 3 |
| 1 | 1 | 2 | 1 | 1 | 1 |
| 1 | 1 | 2 | 1 | 2 | 2 |
| 1 | 1 | 2 | 1 | 3 | 3 |
| 1 | 1 | 2 | 2 | 1 | 1 |
| 1 | 1 | 2 | 2 | 2 | 2 |
| 1 | 1 | 2 | 2 | 3 | 3 |
| 1 | 1 | 2 | 3 | 1 | 1 |
| 1 | 1 | 2 | 3 | 2 | 2 |
| 1 | 1 | 2 | 3 | 3 | 3 |
| 1 | 1 | 3 | 1 | 1 | 1 |
| 1 | 1 | 3 | 1 | 2 | 2 |
| 1 | 1 | 3 | 1 | 3 | 3 |
| 1 | 1 | 3 | 2 | 1 | 1 |
| 1 | 1 | 3 | 2 | 2 | 2 |
| 1 | 1 | 3 | 2 | 3 | 3 |
| 1 | 1 | 3 | 3 | 1 | 1 |
| 1 | 1 | 3 | 3 | 2 | 2 |
| 1 | 1 | 3 | 3 | 3 | 3 |
| 1 | 2 | 1 | 1 | 1 | 1 |
| 1 | 2 | 1 | 1 | 2 | 2 |
| 1 | 2 | 1 | 1 | 3 | 3 |
| 1 | 2 | 1 | 2 | 1 | 1 |
| 1 | 2 | 1 | 2 | 2 | 2 |
| 1 | 2 | 1 | 2 | 3 | 3 |
| 1 | 2 | 1 | 3 | 1 | 1 |
| 1 | 2 | 1 | 3 | 2 | 2 |
| 1 | 2 | 1 | 3 | 3 | 3 |
| 1 | 2 | 2 | 1 | 1 | 1 |
| 1 | 2 | 2 | 1 | 2 | 2 |
| 1 | 2 | 2 | 1 | 3 | 3 |
| 1 | 2 | 2 | 2 | 1 | 1 |
| 1 | 2 | 2 | 2 | 2 | 2 |
| 1 | 2 | 2 | 2 | 3 | 3 |
| 1 | 2 | 2 | 3 | 1 | 1 |
| 1 | 2 | 2 | 3 | 2 | 2 |
| 1 | 2 | 2 | 3 | 3 | 3 |
| 1 | 2 | 3 | 1 | 1 | 1 |
| 1 | 2 | 3 | 1 | 2 | 2 |
| 1 | 2 | 3 | 1 | 3 | 3 |
| 1 | 2 | 3 | 2 | 1 | 1 |
| 1 | 2 | 3 | 2 | 2 | 2 |
| 1 | 2 | 3 | 2 | 3 | 3 |
| 1 | 2 | 3 | 3 | 1 | 1 |
| 1 | 2 | 3 | 3 | 2 | 2 |
| 1 | 2 | 3 | 3 | 3 | 3 |
| 1 | 3 | 1 | 1 | 1 | 2+ |
| 1 | 3 | 1 | 1 | 2 | 2+ |
| 1 | 3 | 1 | 1 | 3 | 3 |
| 1 | 3 | 1 | 2 | 1 | 2+ |
| 1 | 3 | 1 | 2 | 2 | 2+ |
| 1 | 3 | 1 | 2 | 3 | 3 |
| 1 | 3 | 1 | 3 | 1 | 2+ |
| 1 | 3 | 1 | 3 | 2 | 2+ |
| 1 | 3 | 1 | 3 | 3 | 3 |
| 1 | 3 | 2 | 1 | 1 | 2+ |
| 1 | 3 | 2 | 1 | 2 | 2+ |
| 1 | 3 | 2 | 1 | 3 | 3 |
| 1 | 3 | 2 | 2 | 1 | 2+ |
| 1 | 3 | 2 | 2 | 2 | 2+ |
| 1 | 3 | 2 | 2 | 3 | 3 |
| 1 | 3 | 2 | 3 | 1 | 2+ |
| 1 | 3 | 2 | 3 | 2 | 2+ |
| 1 | 3 | 2 | 3 | 3 | 3 |
| 1 | 3 | 3 | 1 | 1 | 2+ |
| 1 | 3 | 3 | 1 | 2 | 2+ |
| 1 | 3 | 3 | 1 | 3 | 3 |
| 1 | 3 | 3 | 2 | 1 | 2+ |
| 1 | 3 | 3 | 2 | 2 | 2+ |
| 1 | 3 | 3 | 2 | 3 | 3 |
| 1 | 3 | 3 | 3 | 1 | 2+ |
| 1 | 3 | 3 | 3 | 2 | 3 |
| 1 | 3 | 3 | 3 | 3 | 3 |
| 2 | 1 | 1 | 1 | 1 | 2 |
| 2 | 1 | 1 | 1 | 2 | 2+ |
| 2 | 1 | 1 | 1 | 3 | 3 |
| 2 | 1 | 1 | 2 | 1 | 2 |
| 2 | 1 | 1 | 2 | 2 | 2+ |
| 2 | 1 | 1 | 2 | 3 | 3 |
| 2 | 1 | 1 | 3 | 1 | 2+ |
| 2 | 1 | 1 | 3 | 2 | 2+ |
| 2 | 1 | 1 | 3 | 3 | 3 |
| 2 | 1 | 2 | 1 | 1 | 2 |
| 2 | 1 | 2 | 1 | 2 | 2+ |
| 2 | 1 | 2 | 1 | 3 | 3 |
| 2 | 1 | 2 | 2 | 1 | 2 |
| 2 | 1 | 2 | 2 | 2 | 2+ |
| 2 | 1 | 2 | 2 | 3 | 3 |
| 2 | 1 | 2 | 3 | 1 | 2+ |
| 2 | 1 | 2 | 3 | 2 | 2+ |
| 2 | 1 | 2 | 3 | 3 | 3 |
| 2 | 1 | 3 | 1 | 1 | 2+ |
| 2 | 1 | 3 | 1 | 2 | 2+ |
| 2 | 1 | 3 | 1 | 3 | 3 |
| 2 | 1 | 3 | 2 | 1 | 2+ |
| 2 | 1 | 3 | 2 | 2 | 2+ |
| 2 | 1 | 3 | 2 | 3 | 3 |
| 2 | 1 | 3 | 3 | 1 | 3 |
| 2 | 1 | 3 | 3 | 2 | 3 |
| 2 | 1 | 3 | 3 | 3 | 3 |
| 2 | 2 | 1 | 1 | 1 | 2+ |
| 2 | 2 | 1 | 1 | 2 | 2+ |
| 2 | 2 | 1 | 1 | 3 | 3 |
| 2 | 2 | 1 | 2 | 1 | 2+ |
| 2 | 2 | 1 | 2 | 2 | 2+ |
| 2 | 2 | 1 | 2 | 3 | 3 |
| 2 | 2 | 1 | 3 | 1 | 2+ |
| 2 | 2 | 1 | 3 | 2 | 2+ |
| 2 | 2 | 1 | 3 | 3 | 3 |
| 2 | 2 | 2 | 1 | 1 | 2+ |
| 2 | 2 | 2 | 1 | 2 | 2+ |
| 2 | 2 | 2 | 1 | 3 | 3 |
| 2 | 2 | 2 | 2 | 1 | 2+ |
| 2 | 2 | 2 | 2 | 2 | 2+ |
| 2 | 2 | 2 | 2 | 3 | 3 |
| 2 | 2 | 2 | 3 | 1 | 3 |
| 2 | 2 | 2 | 3 | 2 | 3 |
| 2 | 2 | 2 | 3 | 3 | 3 |
| 2 | 2 | 3 | 1 | 1 | 2+ |
| 2 | 2 | 3 | 1 | 2 | 3 |
| 2 | 2 | 3 | 1 | 3 | 3 |
| 2 | 2 | 3 | 2 | 1 | 2+ |
| 2 | 2 | 3 | 2 | 2 | 3 |
| 2 | 2 | 3 | 2 | 3 | 3 |
| 2 | 2 | 3 | 3 | 1 | 3 |
| 2 | 2 | 3 | 3 | 2 | 3 |
| 2 | 2 | 3 | 3 | 3 | 3 |
| 2 | 3 | 1 | 1 | 1 | 2+ |
| 2 | 3 | 1 | 1 | 2 | 2+ |
| 2 | 3 | 1 | 1 | 3 | 3 |
| 2 | 3 | 1 | 2 | 1 | 2+ |
| 2 | 3 | 1 | 2 | 2 | 2+ |
| 2 | 3 | 1 | 2 | 3 | 3 |
| 2 | 3 | 1 | 3 | 1 | 2+ |
| 2 | 3 | 1 | 3 | 2 | 3 |
| 2 | 3 | 1 | 3 | 3 | 3 |
| 2 | 3 | 2 | 1 | 1 | 2+ |
| 2 | 3 | 2 | 1 | 2 | 2+ |
| 2 | 3 | 2 | 1 | 3 | 3 |
| 2 | 3 | 2 | 2 | 1 | 2+ |
| 2 | 3 | 2 | 2 | 2 | 2+ |
| 2 | 3 | 2 | 2 | 3 | 3 |
| 2 | 3 | 2 | 3 | 1 | 3 |
| 2 | 3 | 2 | 3 | 2 | 3 |
| 2 | 3 | 2 | 3 | 3 | 3 |
| 2 | 3 | 3 | 1 | 1 | 2+ |
| 2 | 3 | 3 | 1 | 2 | 3 |

-continued

| Risk Behav | Alliance | Soc Perf | Resource | Withdrawal Potential | TREATMENT INTENSITY |
|---|---|---|---|---|---|
| 2 | 3 | 3 | 1 | 3 | 3 |
| 2 | 3 | 3 | 2 | 1 | 2+ |
| 2 | 3 | 3 | 2 | 2 | 3 |
| 2 | 3 | 3 | 2 | 3 | 3 |
| 2 | 3 | 3 | 3 | 1 | 3 |
| 2 | 3 | 3 | 3 | 2 | 3 |
| 2 | 3 | 3 | 3 | 3 | 3 |
| 3 | 1 | 1 | 1 | 1 | 2+ |
| 3 | 1 | 1 | 1 | 2 | 2+ |
| 3 | 1 | 1 | 1 | 3 | 3 |
| 3 | 1 | 1 | 2 | 1 | 2+ |
| 3 | 1 | 1 | 2 | 2 | 2+ |
| 3 | 1 | 1 | 2 | 3 | 3 |
| 3 | 1 | 1 | 3 | 1 | 2+ |
| 3 | 1 | 1 | 3 | 2 | 2+ |
| 3 | 1 | 1 | 3 | 3 | 3 |
| 3 | 1 | 2 | 1 | 1 | 2+ |
| 3 | 1 | 2 | 1 | 2 | 2+ |
| 3 | 1 | 2 | 1 | 3 | 3 |
| 3 | 1 | 2 | 2 | 1 | 2+ |
| 3 | 1 | 2 | 2 | 2 | 2+ |
| 3 | 1 | 2 | 2 | 3 | 3 |
| 3 | 1 | 2 | 3 | 1 | 2+ |
| 3 | 1 | 2 | 3 | 2 | 2+ |
| 3 | 1 | 2 | 3 | 3 | 3 |
| 3 | 1 | 3 | 1 | 1 | 2+ |
| 3 | 1 | 3 | 1 | 2 | 3 |
| 3 | 1 | 3 | 1 | 3 | 3 |
| 3 | 1 | 3 | 2 | 1 | 3 |
| 3 | 1 | 3 | 2 | 2 | 3 |
| 3 | 1 | 3 | 2 | 3 | 3 |
| 3 | 1 | 3 | 3 | 1 | 3 |
| 3 | 1 | 3 | 3 | 2 | 3 |
| 3 | 1 | 3 | 3 | 3 | 3 |
| 3 | 2 | 1 | 1 | 1 | 3 |
| 3 | 2 | 1 | 1 | 2 | 3 |
| 3 | 2 | 1 | 1 | 3 | 3 |
| 3 | 2 | 1 | 2 | 1 | 3 |
| 3 | 2 | 1 | 2 | 2 | 3 |
| 3 | 2 | 1 | 2 | 3 | 3 |
| 3 | 2 | 1 | 3 | 1 | 3 |
| 3 | 2 | 1 | 3 | 2 | 3 |
| 3 | 2 | 1 | 3 | 3 | 3 |
| 3 | 2 | 2 | 1 | 1 | 3 |
| 3 | 2 | 2 | 1 | 2 | 3 |
| 3 | 2 | 2 | 1 | 3 | 3 |
| 3 | 2 | 2 | 2 | 1 | 3 |
| 3 | 2 | 2 | 2 | 2 | 3 |
| 3 | 2 | 2 | 2 | 3 | 3 |
| 3 | 2 | 2 | 3 | 1 | 3 |
| 3 | 2 | 2 | 3 | 2 | 3 |
| 3 | 2 | 2 | 3 | 3 | 3 |
| 3 | 2 | 3 | 1 | 1 | 3 |
| 3 | 2 | 3 | 1 | 2 | 3 |
| 3 | 2 | 3 | 1 | 3 | 3 |
| 3 | 2 | 3 | 2 | 1 | 3 |
| 3 | 2 | 3 | 2 | 2 | 3 |
| 3 | 2 | 3 | 2 | 3 | 3 |
| 3 | 2 | 3 | 3 | 1 | 3 |
| 3 | 2 | 3 | 3 | 2 | 3 |
| 3 | 2 | 3 | 3 | 3 | 3 |
| 3 | 3 | 1 | 1 | 1 | 3 |
| 3 | 3 | 1 | 1 | 2 | 3 |
| 3 | 3 | 1 | 1 | 3 | 3 |
| 3 | 3 | 1 | 2 | 1 | 3 |
| 3 | 3 | 1 | 2 | 2 | 3 |
| 3 | 3 | 1 | 2 | 3 | 3 |
| 3 | 3 | 1 | 3 | 1 | 3 |
| 3 | 3 | 1 | 3 | 2 | 3 |
| 3 | 3 | 1 | 3 | 3 | 3 |
| 3 | 3 | 2 | 1 | 1 | 3 |
| 3 | 3 | 2 | 1 | 2 | 3 |
| 3 | 3 | 2 | 1 | 3 | 3 |
| 3 | 3 | 2 | 2 | 1 | 3 |
| 3 | 3 | 2 | 2 | 2 | 3 |
| 3 | 3 | 2 | 2 | 3 | 3 |
| 3 | 3 | 2 | 3 | 1 | 3 |
| 3 | 3 | 2 | 3 | 2 | 3 |
| 3 | 3 | 2 | 3 | 3 | 3 |
| 3 | 3 | 3 | 1 | 1 | 3 |
| 3 | 3 | 3 | 1 | 2 | 3 |
| 3 | 3 | 3 | 1 | 3 | 3 |
| 3 | 3 | 3 | 2 | 1 | 3 |
| 3 | 3 | 3 | 2 | 2 | 3 |
| 3 | 3 | 3 | 2 | 3 | 3 |
| 3 | 3 | 3 | 3 | 1 | 3 |
| 3 | 3 | 3 | 3 | 2 | 3 |
| 3 | 3 | 3 | 3 | 3 | 3 |

After a recommended treatment intensity has been generated, it is correlated with one of the levels of potential care. If necessary, the treatment determinants may be normed or assigned for groups such as children, adolescents, adults, and substance abuse populations.

The method of the present invention readily lends itself to use with a central processing unit (CPU) or computer. For example, a database containing a series of questions relating to the clinical data to be collected and containing case history information and treatment intensity information for different categories of patients such as children, adolescent, adults and substance abusers may be provided. The database may be stored in a memory section of the CPU or computer or in a separate storage device to which the CPU or computer has access.

The CPU or computer may be used to record the answers to the questions being asked to an individual. If desired, the computer can be programmed to select questions from the database based upon recorded or inputted answers.

The computer may also be programmed to automatically generate the behavioral severity series for the individual whose case is being evaluated as well as derive a recommended treatment intensity. The computer may also be programmed to compare the recommended treatment intensity with archival or historical data about recommended treatment intensities for a particular class of individuals or patients stored in the database.

Any computer language known in the art may be used to program the computer. If desired, artificial intelligence or expert system technology may be used to allow the computer to select the questions to be asked to a particular individual and to evaluate the responses to the questions. The following is an example of how the method of the present invention may be used as part of a precertification review.

The patient is a 26 year old married woman who works as a marketing assistant in a manufacturing company. She never had any psychiatric problems until three weeks previously when she began experiencing sleep disturbance, somatic concerns, loss of energy and appetite and depressed mood. Her primary care physician recognized the symptoms of depression, ruled out medical conditions and referred her to an HMO participating physician. Upon evaluating the patient, he recommended admission to a hospital.

A precertification review was conducted using the method of the present invention. An interview with the patient determined the following:

the patient had not exhibited any suicidal behavior, plan or ideation. Danger Rating=1;

the psychiatrist was not sure if she was a risk for suicide—his uncertainty was based on the patient's statement "I wish that I would just fall asleep and die"; and the severity of the depressive symptoms. The psychiatrist felt that inpatient monitoring was needed. Provider Opinion Rating=2;

the psychiatrist described the patient as able to communicate clearly and as having no problems in relationship to her husband. To date, she has been able to attend work regularly, but she has to go to the ladies room when she experiences crying episodes. Social Performance Rating=1;

her husband is capable of helping her but travels and therefore is not available on a full time basis to provide support. Social Resources Rating=2; and she denied substance abuse and shows no signs of same. Substance Abuse Risk=1.

The patient's behavioral series is 1-2-1-2-1. This profile correlates with a treatment intensity of "low intensity diversion", i.e., the patient was diverted from inpatient care and instead attended an outpatient program in the evening 3 hours a day for 5 nights where mental health professionals monitored her suicidal risk and provided treatment in the form of medication and cognitive therapy. After two weeks of this intervention, the depression disappeared and weekly treatment with a psychiatrist began.

As a result of this review, a cost saving was effected for the HMO and valuable inpatient resources were conserved.

As can be seen from the foregoing example, the method of the present invention (a) insures that reliable and valid clinical guidelines for the assignment of care are applied; (b) reduces unnecessary and ineffective care; (c) insures that the appropriate intensity of care is provided; and (d) provides an objective, verifiable audit and database of the clinical decision making process for quality management and outcome research purposes. This is because the method provides an objective tool to analyze clinical data and a normative database against which to evaluate treatment options to allow allocation of care. A particular advantage to the method of the present invention is its ability to identify medically unnecessary treatment.

It is apparent that there has been provided in accordance with this invention a method for evaluating and reviewing a patient's condition which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A computer-assisted method for evaluating and reviewing the condition of an individual and a proposed level of care for said individual, said method comprising the steps of:

collecting clinical data relevant to a determination of the necessity of said proposed level of care;

said collecting step comprises gathering information about a plurality of elements including said individual's behavior, a provider's opinion as to imminent danger, and social resources available to the individual;

recording said gathered information by inputting said information into a computer;

generating a behavioral severity series for said individual from said recorded information;

said generating step comprising respective rating of each of said elements on a scale having a defined range;

deriving a treatment intensity based upon said behavioral severity series; and said deriving step comprising deriving a recommended treatment intensity from a matrix which takes into account said rating for each said element and a weighing of said respective ratings.

2. The method of claim 1 wherein said information gathering step comprises gathering information about the individual's tendency towards dangerous behavior, the individual's social performance, and the individual's substance abuse risk.

3. The method of claim 1 wherein each said scale has a range of 1 to 3.

4. The method of claim 1 wherein said treatment deriving intensity step comprises identifying different levels of potential care for an individual and correlating said recommended treatment with one of said levels of potential care.

5. The method of claim 4 wherein said different levels of care include: (a) standard outpatient care; (b) high intensity outpatient care; (c) standard diversion care; (d) high intensity diversion care including partial hospitalization; (e) holding bed care; (f) residential, non-hospital; and (g) inpatient care.

6. The method of claim 4 wherein said different levels of care in the case of substance abuse illnesses include: (a) standard outpatient care; (b) high intensity outpatient care; (c) medically managed outpatient care; (d) high intensity diversion care; (e) residential therapeutic community care; and (f) inpatient detoxification care.

7. The method of claim 4 wherein said treatment intensity deriving step further comprises norming said behavioral severity series for at least one factor selected from the group consisting of: (a) child; (b) adolescent; (c) adult; and (d) substance abuse populations.

8. The method of claim 4 further comprising:

providing a database containing case history information and treatment intensity information for individuals stored on a storage device; and comparing said recommended treatment intensity with treatment information within said database.

9. A method for assessing and reviewing the condition of an individual and a proposed level of care for said individual, said method comprising the steps of:

providing a computer;

providing a database on a storage device which contains a number of potential questions which can be asked as part of a clinical data collecting step;

collecting clinical data relevant to a determination of the necessity of said proposed level of care by gathering information about the behavior of said individual, a provider's opinion as to imminent danger, and social resources available to said individual;

inputting said gathered information into said computer;

selecting questions from said database in response to said inputted information;

generating a behavioral severity series for said individual from said gathered information and responses to said selected questions; and deriving a treatment intensity for said individual using a matrix which takes into account said behavioral severity series.

10. The method of claim 9 wherein said selecting step is performed by said central processing unit.

11. The method of claim 9 further comprising:

storing said gathered information and said derived treatment intensity in said database.

12. The method of claim 9 further comprising:

said driving step comprising deriving a recommended treatment intensity; and comparing said recommended treatment intensity with archival data about recommended treatment intensities for a particular class of individuals stored in said database.

13. The method of claim 9 wherein said clinical data collecting step comprises gathering information about the individual from a treating clinician.

14. The method of claim 9 wherein said clinical data collecting step comprises gathering information about the individual from a psychiatrist.

15. The method of claim 9 wherein said behavioral severity series is generated by said computer.

16. The method of claim 9 wherein said treatment intensity is derived by said computer.

* * * * *